United States Patent [19]

Lacefield et al.

[11] Patent Number: 4,508,735
[45] Date of Patent: Apr. 2, 1985

[54] ANTI-ARRHYTHMIC N-ALKANOYLAMINOALKYL FLUORENES

[75] Inventors: William B. Lacefield; Terry D. Lindstrom, both of Indianapolis, Ind.

[73] Assignee: Eli Lilly and Company, Indianapolis, Ind.

[21] Appl. No.: 534,519

[22] Filed: Sep. 21, 1983

[51] Int. Cl.³ .................. C07C 103/28; A61K 31/165
[52] U.S. Cl. .............................. 514/616; 260/465 D; 560/41; 562/442; 562/450; 564/155; 564/164; 564/219; 514/617; 514/629; 514/521; 514/530
[58] Field of Search .............. 424/324, 304, 309, 317; 564/155, 164, 219; 560/41; 562/450, 442; 260/465 D

[56] References Cited

U.S. PATENT DOCUMENTS

| | | | |
|---|---|---|---|
| 3,609,179 | 9/1971 | Cavalla et al. | 424/324 |
| 4,197,313 | 4/1980 | Lacefield et al. | 424/304 |
| 4,277,495 | 7/1981 | Lacefield et al. | 424/309 |
| 4,282,170 | 8/1981 | Lavagnino et al. | 424/324 |
| 4,382,093 | 5/1983 | Lacefield et al. | 424/324 |
| 4,452,745 | 6/1984 | Lacefield et al. | 564/164 |

OTHER PUBLICATIONS

Severin et al., *Chemische Berichte* 110.491–110.499 (1977).
Stamm et al., *Chemische Berichte* 111.2665–111.2676 (1978).

*Primary Examiner*—Thomas A. Waltz
*Assistant Examiner*—Carolyn S. Greason
*Attorney, Agent, or Firm*—Charles W. Ashbrook; Arthur R. Whale

[57] ABSTRACT

9-(N-alkanoylaminoalkyl)-fluorenes are anti-arrhythmic agents.

20 Claims, No Drawings

ANTI-ARRHYTHMIC N-ALKANOYLAMINOALKYL FLUORENES

BACKGROUND OF THE INVENTION

This invention concerns certain derivatives of fluorenes that are useful as antiarrhythmic agents.

U.S. Pat. Nos. 4,197,313 and 4,277,495 describe various 9-aminoalkylfluorene derivatives that are useful as antiarrhythmic agents. All of the disclosed compounds are primary, secondary or tertiary amines, or acid addition salts thereof. It has long been known that many antiarrhythmic agents also have local anesthetic activity, and that the cardiac activity of such compounds may in some way be associated with the local anesthetic properties. It has been thought that in order to have anesthetic and/or antiarrhythmic activity, an amino compound had to be basic, ie. a primary, secondary or tertiary amine. Accordingly, no non-basic aminoalkyl fluorene antiarrhythmic agents have heretofore been known.

An object of this invention is to provide a group of non-basic N-alkanoyl-aminoalkylfluorenes that are active as antiarrhythmic agents.

SUMMARY OF THE INVENTION

This invention concerns a group of non-basic 9-aminoalkyl fluorene derivatives. The invention provides compounds having the formula

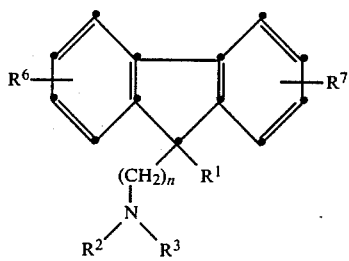

wherein:
$R^1$ is hydroxy, cyano, $CONR^4R^5$ or $COOR^4$ in which $R^4$ and $R^5$ independently are hydrogen or $C_1$–$C_6$ alkyl;
n is 3, 4 or 5;
$R^2$ is hydrogen, $C_1$–$C_6$ alkyl, $CH_2C_2$–$C_5$ alkenyl or phenyl-$C_1$–$C_3$ alkyl;
$R^3$ is $C_1$–$C_6$ alkanoyl, and
$R^6$ and $R^7$ independently are hydrogen, $C_1$–$C_4$ alkyl or halogen.

In a preferred embodiment there is provided compounds of the above formula wherein $R^1$ is $CONH_2$, n is 3 and $R^2$ is $C_1$–$C_6$ alkyl.

Additionally provided by this invention is a pharmaceutical formulation comprising a compound of the above formula admixed with a pharmaceutical carrier or excipient therefor.

This invention also provides a method of treating cardiac arrhythmias comprising administering to a subject an antiarrhythmic amount of a compound of the above formula.

DETAILED DESCRIPTION OF THE INVENTION

The fluorene 9-substitutent defined in the above formula by $R^1$ is hydroxy, cyano, $CONR^4R^5$ or $COOR^4$. Within this term, $R^4$ and $R^5$ independently are hydrogen or $C_1$–$C_6$ alkyl. The term "$C_1$–$C_6$ alkyl" as used herein means a straight or branched carbon chain such as methyl, ethyl, isopropyl, n-butyl, n-hexyl, 1-methylpentyl and the like.

The compounds of this invention are 9-alkylfluorene derivatives, wherein the alkyl chain bears a substituted or disubstituted amino group on the terminal carbon atom. The nitrogen substituents are defined by $R^2$ and $R^3$, wherein $R^2$ is hydrogen, alkyl, $CH_2C_2$–$C_5$ alkenyl such as allyl, 3-hexenyl, 2-pentenyl or 3-butenyl; or phenyl-$C_1$–$C_3$ alkyl such as benzyl, 2-phenylethyl, or 3-phenylpropyl. $R^3$ in the above formula defines a $C_1$–$C_6$ alkanoyl group, which means the acyl residue of a straight or branched chain $C_1$–$C_6$ alkanoic acid. Typical $C_1$–$C_6$ alkanoyl groups include formyl, acetyl, propionyl, 2-methylbutyryl, 3-methylpentanoyl and the like.

$R^6$ and $R^7$ in the above formula are substituents on the aromatic rings of the fluorene nucleus, and are hydrogen, $C_1$–$C_4$ alkyl such as methyl, ethyl, isopropyl or tert.-butyl, or halo. The term "halo" carries its art recognized meaning and includes fluoro, chloro, bromo and iodo.

The compounds provided by this invention can be prepared by general methods such as those disclosed in U.S. Pat. No. 4,197,313. The compounds preferably are prepared by simply acylating a 9-(aminoalkyl or N-substituted aminoalkyl)fluorene with a $C_1$–$C_6$ alkanoyl acylating agent according to the following scheme

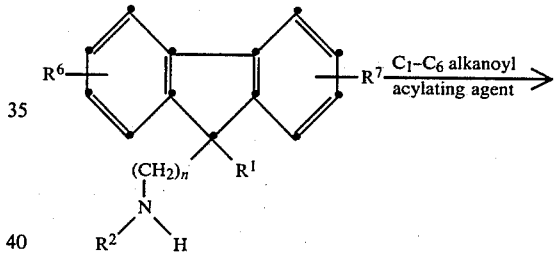

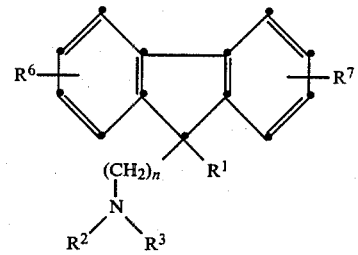

The acylation reaction is accomplished by combining approximately equimolar quantities of the fluorene starting material and the acylating agent. An excess of acylating agent can be employed if desired to ensure complete reaction. Typical acylating agents commonly employed include $C_1$–$C_6$ alkanoic acid anhydrides and mixed anhydrides, for instance formic-hexanoic anhydride; $C_1$–$C_6$ alkanoic acid halides such as acetyl chloride, propionyl bromide, pentanoyl bromide and the like; $C_1$–$C_6$ alkanoic acid amides such as formamide, acetamide, propionamide, butyramide; and related $C_1$–$C_6$ alkanoyl acylating agents.

The acylation reaction can be carried out in an organic solvent if desired. Common laboratory solvents that can be employed include benzene, toluene, pyridine, dichloromethane, xylene, dimethyl sulfoxide and the like. Ideally the reaction is simply carried out using an excess of the acylating agent as the solvent medium. If desired a base such as pyridine or triethylamine can be employed to act as acid scavenger.

The reaction typically is conducted at a temperature of about 30° to about 200° C., and at such temperature the acylation generally is substantially complete after about one to about twenty-four hours. The product can be isolated and purified by standard procedures, including extraction into organic solvents, chromatography, crystallization and the like.

Examples of typical compounds and classes of compounds provided by this invention are included within the following list:

A. Those of the formula

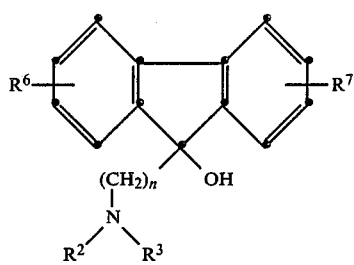

1. n is 3, $R^6$ and $R^7$ both are hydrogen;
    a. $R^2$ is hydrogen
    1 a. 1. $R^3$ is formyl;
    1 a. 2. $R^3$ is acetyl;
    1 a. 3. $R^3$ is isobutyryl;
        b. $R^2$ is methyl;
    1 b. 1. $R^3$ is n-hexanoyl;
    1 b. 2. $R^3$ is 2-methylpentanoyl;
        c. $R^2$ is allyl;
    1 c. 1. $R^3$ is formyl;
    1 c. 2. $R^3$ is acetyl;
        d. $R^2$ is benzyl;
    1 d. 1. $R^3$ is propionyl;
    1 d. 2. $R^3$ is isopentanoyl;
2. n is 4, $R^6$ is 2-chloro and $R^7$ is 7-methyl;
    a. $R^2$ is isopropyl;
    2 a. 1. $R^3$ is formyl;
    2 a. 2. $R^3$ is n-hexanoyl;

B. Those of the formula

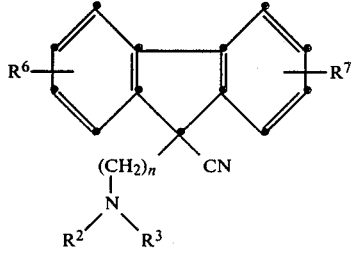

1. n is 3, $R^6$ and $R^7$ both are hydrogen;
    a. $R^2$ is hydrogen;
    1 a. 1. $R^3$ is acetyl;
    1 a. 2. $R^3$ is isobutyryl;
        b. $R^2$ is 3-hexenyl;
    1 b. 1. $R^3$ is formyl;
        c. $R^2$ is 3-phenylpropyl;
    1 c. 1. $R^3$ is propionyl;
    1 c. 2. $R^3$ is pentanoyl;

2. n is 5, $R^6$ and $R^7$ both are fluoro;
    a. $R^2$ is n-hexyl;
    2 a. 1. $R^3$ is formyl;
    2 a. 2. $R^3$ is acetyl;
    2 a. 3. $R^3$ is isopentanoyl;

C. Those of the formula

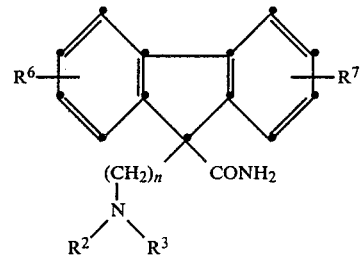

1. n is 3, $R^6$ and $R^7$ both are hydrogen;
    a. $R^2$ is hydrogen;
    1 a. 1. $R^3$ is acetyl;
        b. $R^2$ is n-propyl;
    1 b. 1. $R^3$ is formyl;
    1 b. 2. $R^3$ is propionyl;
        c. $R^2$ is isopropyl;
    1 c. 1. $R^3$ is acetyl;
    1 c. 2. $R^3$ is n-butyryl;
    1 c. 3. $R^3$ is isobutyryl;
    1 c. 4. $R^3$ is n-hexanoyl;
2. n is 4, $R^6$ is hydrogen, $R^7$ is 1-bromo;
    a. $R^2$ is benzyl;
    2 a. 1. $R^3$ is formyl;
    2 a. 2. $R^3$ is acetyl;
        b. $R^2$ is allyl;
    2 b. 1. $R^3$ is propionyl;
    2 b. 2. $R^3$ is isopentanoyl;

D. Those of the formula

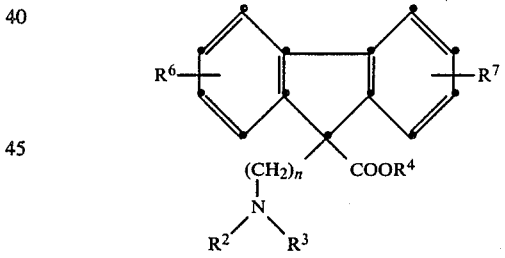

1. n is 3, $R^6$ and $R^7$ both are hydrogen, $R^4$ is methyl;
    a. $R^2$ is isopropyl;
    1 a. 1. $R^3$ is n-butyryl;
    1 a. 2. $R^3$ is n-hexanoyl;
        b. $R^2$ is 4-hexenyl;
    1 b. 1. $R^3$ is acetyl.

The synthesis of the compounds provided by this invention is more fully illustrated by the following working examples.

EXAMPLE 1

9-Carbamoyl-9-[3(N-formyl-N-isopropyl)aminopropyl]fluorene

A mixture of 4.0 g (13 mM) of 9-carbamoyl-9-(3-isopropylaminopropyl)fluorene and 4.5 g (100 mM) of formamide was stirred at 160° C. for two hours. The reaction mixture was cooled to 30° C. and added to 100 ml of water and 100 ml of ethyl acetate. The organic layer was separated, washed twice with 50 ml portions of 6N hydrochloric acid and then twice with 50 ml portions of water, and dried. Removal of the solvent by evaporation under reduced pressure afforded an oil. The oil was purified by chromatography over silica gel, eluting with ethyl acetate. The fractions shown by thin layer chromatography (98% v/v methanol-dichloromethane) to have an $R_f$ of 0.11 were combined and concentrated to dryness to give 1.9 g of 9-carbamoyl-9-[3-(N-formyl-N-isopropyl)aminopropyl]fluorene. mp 113°–115° C. Analysis calcaluated for $C_{21}H_{24}N_2O_2$ Theory: C, 74.97; H, 7.19; N, 8.33.
Found: C, 74.75; H, 7.31; N, 8.25.
NMR (CDCl$_3$): $\delta$1.0 (m, 7H); 2.4 (m, 2H); 2.9 (m, 2H); 3.5 (m, 1H); 5.1 (broad d, 2H); 7.2–8.0 (m, 8H).

EXAMPLE 2

9-Carbamoyl-9-(3-formamidopropyl)-fluorene

To a stirred hot (50° C.) solution of 6.2 g (23 mM) of 9-carbamoyl-9-(3-aminopropyl)fluorene in 50 ml of 98% formic acid were added dropwise over ten minutes 17 ml of acetic anhydride. The reaction mixture was cooled to about 30° C. and stirred for one hour, and then added to 100 ml of ice water. The aqueous mixture was diluted by addition of 100 ml of ethyl acetate, and the organic layer was separated, washed with two 50 ml portions of 5% w/v aqueous sodium bicarbonate, twice with 5 ml portions of 1N hydrochloric acid, again with sodium bicarbonate, and finally with water. The solution was dried and the solvent was removed by evaporation under reduced pressure to provide 2.0 g of 9-carbamoyl-9-(3-formamidopropyl)fluorene. mp 160°–161° C.

Analysis calc. for $C_{18}H_{18}N_2O_2$: Theory: C, 73.45; H, 6.16; N, 9.52. Found: C, 73.24; H, 6.44; N, 9.79.
IR (CHCl$_3$): 1686 cm$^{-1}$, 1578 cm$^{-1}$.
NMR (DMSOd$_6$): $\delta$0.5–1.0 (m, 2H); 2.0–2.7 (m, 2H) 2.9 (q, 2H); 6.1 and 6.9 (two 5, 2H) 7.3–8.2 (m, 9H).
Mass Spec Theory 294; M+ 294.
Titration showed no titratable group.

EXAMPLE 3

9-Carbamoyl-9-[3-(N-acetyl-N-isopropyl)aminopropyl]fluorene

To a stirred solution of 6.9 g (20 mM) of 9-carbamoyl-9-(3-isopropylaminopropyl)fluorene hydrochloride in 25 ml of pyridine were added 1.5 g (20 mM) of acetyl chloride. The reaction mixture was stirred at 25° C. for three hours and then added to 100 ml of water. The aqueous mixture was extracted several times with ethyl acetate. The organic extracts were combined, washed with 10% w/v aqueous sodium hydroxide, twice with 50 ml portions of 1N hydrochloric acid and dried. Removal of the solvent by evaporation under reduced pressure provided 4.2 g of an oil which, following purification by chromatography was identified as 9-carbamoyl-9-[3-(N-acetyl-N-isopropyl)aminopropyl]fluorene.

Analysis calc. for $C_{22}H_{26}N_2O_2$: Theory: C, 73.51; H, 7.57; N, 7.79; O, 11.13. Found: C, 73.50; H, 7.08; N, 7.35; O, 11.27.

Mass Spec. M+ Theory 351, Found 351.
Titration showed no titratable group.
IR(CHCl$_3$): 1680, 1621 cm$^{-1}$.
NMR(CDCl$_3$): $\delta$0.82(S, 3H); 0.90(S, 3H); 0.7–1.1(m, 2H); 1.9(d, 3H); 2.45(m, 2H); 2.9(m, 2H); 3.8 and 4.5(two m, 1H); 4.9–5.1(m, 2H); 7.2–7.9(m, 8H).

EXAMPLE 4

By following the general procedure of Examples 1–3, the following N-alkanoyl aminoalkylfluorenes are prepared from the corresponding 9-aminoalkylfluorene derivative:

9-cyano-9-(4-butyramidobutyl)fluorene;
9-ethoxycarbonyl-9-[3-(N-acetyl-N-isohexyl)aminopropyl]fluorene;
9-hydroxy-9-[5-(N-propionyl-N-allyl)aminopentyl]fluorene;
9-N,N-diethylcarbamoyl-9-[3-(N-hexanoyl-N-methyl)aminopropyl]fluorene; and
2,7-difluoro-9-carbamoyl-9-(3-acetamidopropyl)fluorene.

The N-alkanoyl aminoalkylfluorenes provided by this invention are useful as intermediates leading to antiarrhythmic agents, and are also useful as anti-arrhythmic agents and per se can be employed in the prophylactic and therapeutic treatment of conditions of irregular heartbeat in animals. The antiarrhythmic activity of the compounds has been demonstrated in standard in vivo animal tests. The tests comprise administering a compound of the invention to an animal suffering from an experimentally induced cardiac arrhythmia and observing whether the compound effects a conversion of the arrhythmia to a normal sinus rhythum, and if so, by measuring the duration of the conversion.

In a typical experiment to determine the activity of the compounds of this invention, dogs of either sex were anesthetized with sodium pentobarbital (35 mg/kg) and respired through a cuffed endotracheal tube. Body temperature was maintained at 37°–38° C. using a water heated pad. The lead II electrocardiogram was obtained using subdermal needle electrodes and a Beckman strip-chart recorder. A 21 gauge butterfly infusion needle was placed in the cephalic vein. For experiments in which compounds were given intraduodenally, the abdomen was opened along the midline and a section of duodenum approximately 10 cm below the pyloric sphincter was isolated. An incision was made in the duodenum, a silastic tube was inserted and a purse-string suture closed about the tube. The abdomen was then closed.

Quabain (50 $\mu$g/kg) was given, followed every 15 min thereafter by 5 $\mu$g/kg supplemental doses of ouabain until an arrhythmia appeared. Abnormal beats were identified by an abnormal configuration of the QRS complex, long QRS duration and by an absence of coupled P waves. If a few but less than 50 percent abnormal beats were present or if the arrhythmia did not persist for 30 min, an additional 2.5 $\mu$g/kg dose of ouabain was administered. Following 30 continuous minutes of arrhythmia, test compounds were administered.

For intraduodenal administration, the compound of Example 1 was suspended in 10 percent acacia and given in 10 ml followed by a 3 ml flush. Lead II ECG was monitered for 2 hr. For intravenous administraiton, the compound of Example 1 was dissolved in polyethylene glycol 300 and infused at 0.01 ml/kg/min. ECG was monitored during infusion and when the arrhythmia reverted to 100 percent sinus beats, the dose administered was noted. Infusion was continued up to twice this dose or for a total of 50 min.

The result of the in vivo test as outlined above for the compound of Example 1 are presented in Tables 1 and 2.

TABLE 1

Percent Sinus Beats in Ouabain Intoxicated Dogs Following Intraduodenal Administration of Compound of Example 1.

| | Mean Percent Sinus Beats | | | |
|---|---|---|---|---|
| Minutes | 1 mg/kg | 2 mg/kg | 2.5 mg/kg | 5 mg/kg |
| 0 | 5 | 4 | 0 | 19 |
| 10 | 4 | 30 | 0 | 17 |
| 20 | 2 | 30 | 0 | 23 |
| 30 | 16 | 28 | 3 | 38 |
| 40 | 5 | 26 | 9 | 100 |
| 50 | 0 | 26 | 11 | 100 |
| 60 | 0 | 34 | 15 | 100 |
| 90 | 0 | 74 | 100 | 100 |
| 120 | 0 | 65 | 100 | 100 |
| (n) | 2 | 2 | 1 | 2 |

TABLE 2

Effect of Intravenous Infusion of Compound of Example 1 (100 μg/kg/min) in Ouabin Intoxicated Dogs.

| Minutes[b] | Dose (mg/kg) | Sinus Beats | Ectopic Beats | Total Beats | Percent Sinus Beats |
|---|---|---|---|---|---|
| −50 | 0 | 0 | 198 | 198 | 0 |
| −40 | 1 | 0 | 188 | 188 | 0 |
| −30 | 2 | 0 | 186 | 186 | 0 |
| −20 | 3 | 0 | 172 | 172 | 0 |
| −10 | 4 | 94[c] | 84 | 178 | 50 |
| 0 | 5 | 174[c] | 0 | 174 | 100 |
| 10 | — | 174[c] | 0 | 174 | 100 |
| 40 | — | 164[c] | 0 | 164 | 100 |
| 70 | — | 158[c] | 0 | 158 | 100 |

[a]Values are means from 2 dogs.
[b]Drug infusion was from −50 to 0 min.
[c]Rhythm could not be clearly identified as sinus rhythm in one of the two dogs but, rather, this may have been a junctional rhythm.

The data presented in Tables 1 and 2 demonstrates that the compounds of this invention have useful antiarrhythmic activity when evaluated in the ouabain intoxication model. The compound of Example 1 was further evaluated in the Harris dog model (coronary artery ligation model) and failed to demonstrate observable anti-arrhythmic activity. Because the compound demonstrated such excellent activity in the standard ouabain model, it is contemplated that the compounds of the invention will be useful in the treatment of humans for conditions of irregular heart beat.

The treatment of animals suffering from a cardiac arrhythmia or suspected of developing a cardiac arrhythmia employing an N-alkanoylaminoalkylfluorene as defined herein is provided as an additional embodiment of this invention.

According to the method of this invention, the 9-aminoalkylfluorenes of the above formula are employed in combatting cardiac arrhythmias in animals by administering an antiarrhythmic amount of one or more of the aminoalkylfluorenes to an animal. The compounds are effective as antiarrhythmic agents when administered internally to an animal so as to introduce the compound into the animal's cardiovascular system. Parenteral administration of the compounds can be accomplished by intraperitoneal, subcutaneous or intravenous injection. The compounds alternatively can be administered orally in the form of tablets, capsules, elixirs, syrups, buccal seals and the like. The aminoalkylfluorenes have good antiarrhythmic activity both therapeutically, for instance when administered to an animal suffering from an arrhythmia and in need of treatment, and prophylactically when administered to an animal suspected of developing an arrhythmia, thereby protecting the animal against the occurrence or recurrence of arrhythmias.

The 9-aminoalkylfluorenes generally are utilized as pharmaceutical formulations. Such formulations ideally contain from about 1 to about 90 percent by weight of an aminoalkylfluorene in combination with a suitable pharmaceutical diluent, excipient or carrier therefor. Diluents commonly utilized in formulating the compounds in solid form suitable for oral administration include starch, lactose, gelatin, silica gel, rice flour, carboxymethyl cellulose and the like. Carriers and excipients employed in liquid formulations suitable for parenteral administration via the intravenous, intramuscular, or subcutaneous routes include water, saline, glucose syrup, ethanol, corn oil and the like.

The 9-aminoalkylfluorenes can be administered to a subject suffering from an arrhythmia and in need of treatment, or to a subject suspected of developing an arrhythmia and in need of prophylactic treatment. Parenteral administration may be preferred for subjects suffering from a life-threatening arrhythmia. Oral administration generally is preferred for maintenance or prophylactic treatment. The compounds ideally are formulated in such a way that the effective dose of 9-aminoalkylfluorene is an amount sufficient to treat the arrhythmia. Such doses typically will be from about 0.05 to about 25 mg/kg. A typical oral dose for the treatment of a patient suffering from an arrhythmia and weighing about 70 kg will be, for example, from about 3.5 to about 400 mg of a suitably formulated aminoalkylfluorene, for instance 9-carbamoyl-9-[3-(N-formyl-N-isopropyl)aminopropyl]fluorene. Such oral dosing may be made from 1 to about 4 times each day, or as dictated by the particular patient and condition being treated. Such compound can of course be formulated for parenteral administration, for instance by intravenous infusion. Such formulation can be prepared by dissolving about 500 mg of the above-noted or related compound in a suitable diluent such as 1000 ml of 5 percent glucose. Such solution can be infused into a patient suffering from an arrhythmia at the rate of about 1 ml per minute.

We claim:
1. An N-alkanoylaminoalkylfluorene of the formula

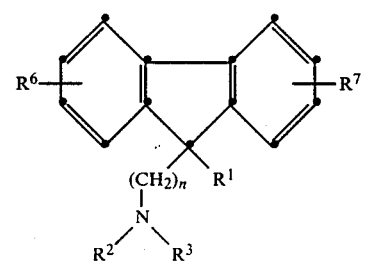

wherein:
$R^1$ is hydroxy, cyano, $CONR^4R^5$ or $COOR^4$, in which $R^4$ and $R^5$ independently are hydrogen or $C_1-C_6$ alkyl;
n is 3, 4 or 5;
$R^2$ is hydrogen, $C_1-C_6$ alkyl, $CH_2C_2-C_5$ alkenyl or phenyl-$C_1-C_3$ alkyl;
$R^3$ is $C_1-C_6$ alkanoyl; and
$R^6$ and $R^7$ independently are hydrogen, $C_1-C_4$ alkyl or halogen.

2. The compound of claim 1 wherein $R^1$ is $CONR^4R^5$.

3. The compound of claim 2 wherein $R^4$ and $R^5$ both are hydrogen.

4. The compound of claim 3 wherein n is 3.

5. The compound of claim 4 wherein $R^2$ is $C_1$-$C_6$ alkyl.

6. The compound of claim 5 wherein $R^6$ and $R^7$ both are hydrogen.

7. The compound of claim 6 wherein $R^3$ is formyl.

8. The compound of claim 6 wherein $R^3$ is acetyl.

9. A pharmaceutical formulation comprising an effective antiarrhythmic amount of the compound of claim 1 admixed with a pharmaceutical carrier or excipient.

10. The formulation of claim 9 employing a compound wherein $R^1$ is $CONH_2$ and n is 3.

11. The formulation of claim 10 employing a compound wherein $R^6$ and $R^7$ both are hydrogen.

12. The formulation of claim 11 employing a compound wherein $R^2$ is $C_1$-$C_6$ alkyl.

13. The formulation of claim 12 employing a compound wherein $R^2$ is isopropyl.

14. The formulation of claim 13 employing a compond wherein $R^3$ is formyl.

15. The formulation of claim 13 employing a compound wherein $R^3$ is acetyl.

16. A method of treating cardiac arrhythmias comprising administering to a subject an antiarrhythmic amount of a compound of claim 1.

17. The method according to claim 16 employing a compound wherein $R^1$ is $CONH_2$.

18. The method according to claim 17 employing a compound wherein $R^6$ and $R^7$ both are hydrogen.

19. The method according to claim 18 employing a compound wherein n is 3 and $R^2$ is $C_1$-$C_6$ alkyl.

20. The method according to claim 19 employing a compound wherein $R^3$ is formyl or acetyl.

* * * * *